United States Patent
Hino (10) Patent No.: US 9,949,614 B2
(45) Date of Patent: Apr. 24, 2018

(54) DIAL UNIT AND INTRODUCTION APPARATUS

(71) Applicant: OLYMPUS CORPORATION, Tokyo (JP)

(72) Inventor: Kazuhiko Hino, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/353,806

(22) Filed: Nov. 17, 2016

(65) Prior Publication Data
US 2017/0065150 A1 Mar. 9, 2017

Related U.S. Application Data

(63) Continuation of application No. PCT/JP2015/074694, filed on Aug. 31, 2015.

(30) Foreign Application Priority Data

Nov. 12, 2014 (JP) ................................. 2014-230114

(51) Int. Cl.
*A61B 1/00* (2006.01)
*A61B 1/005* (2006.01)
(Continued)

(52) U.S. Cl.
CPC ........ *A61B 1/00002* (2013.01); *A61B 1/0016* (2013.01); *A61B 1/0051* (2013.01);
(Continued)

(58) Field of Classification Search
CPC ..... A61B 1/00002; A61B 1/0051; A61B 1/04; A61B 1/06; A61B 1/0057; A61B 1/0016;
(Continued)

(56) References Cited

U.S. PATENT DOCUMENTS

2007/0255104 A1* 11/2007 Maruyama ........... A61B 1/0052 600/148
2014/0135580 A1* 5/2014 Omoto ................. A61B 1/0052 600/148

FOREIGN PATENT DOCUMENTS

| CN | 104135907 A | 11/2014 |
|---|---|---|
| JP | 2009-207788 A | 9/2009 |

(Continued)

OTHER PUBLICATIONS

English translation of International Preliminary Report on Patentability dated May 26, 2017 together with the Written Opinion received in related International Application No. PCT/JP2015/074694.

(Continued)

*Primary Examiner* — Timothy J Neal
(74) *Attorney, Agent, or Firm* — Scully, Scott, Murphy & Presser, P.C.

(57) ABSTRACT

The dial unit includes a dial including a shaft and being rotatable around the shaft, a detector to detect a rotation amount of the dial, a rotator engaged with the dial and rotatable together with the dial. The dial unit includes a rotation transmission member to keep the dial and the rotator separated from each other before the rotation angle of the dial reaches a first angle and to transmit rotation of the dial to the rotator when the rotation angle exceeds the first angle. The dial unit includes an elastic member which is shaped as a coil-shaped portion and contains the rotator inside the coil-shaped portion. The elastic member applies to the rotator a torque in an opposite direction to a rotational direction of the rotator when the rotator rotates.

6 Claims, 11 Drawing Sheets

(51) Int. Cl.
　　　*A61B 1/04*　　　(2006.01)
　　　*A61B 1/06*　　　(2006.01)
(52) U.S. Cl.
　　　CPC .......... *A61B 1/0052* (2013.01); *A61B 1/0055*
　　　　　(2013.01); *A61B 1/0057* (2013.01); *A61B*
　　　　　*1/00091* (2013.01); *A61B 1/04* (2013.01);
　　　　　　　　　　　　　　　*A61B 1/06* (2013.01)
(58) Field of Classification Search
　　　CPC . A61B 1/0052; A61B 1/0055; A61B 1/00091;
　　　　　　　　　　　　　　　　　A61B 1/00066
　　　See application file for complete search history.

(56) References Cited

FOREIGN PATENT DOCUMENTS

WO　　WO 2013/129494 A1　　9/2013
WO　　WO 2014/123135 A1　　8/2014

OTHER PUBLICATIONS

International Search Report dated Nov. 24, 2015 issued in PCT/JP2015/074694.
Chinese Office Action dated Jul. 25, 2017 in Chinese Patent Application No. 201580027258.3.

\* cited by examiner

DIAL UNIT AND INTRODUCTION APPARATUS

CROSS-REFERENCE TO RELATED APPLICATIONS

This application is a Continuation application of PCT Application No. PCT/JP2015/074694, filed Aug. 31, 2015 and based upon and claiming the benefit of priority from prior the Japanese Patent Application No. 2014-230114, filed Nov. 12, 2014, the entire contents of all of which are incorporated herein by references.

BACKGROUND OF THE INVENTION

1. Field of the Invention

The present invention relates to an introduction apparatus to be inserted into a cavity, and to a dial unit provided for the introduction apparatus.

2. Description of the Related Art

In general, an introduction apparatus to be inserted into a cavity, such as an endoscope, comprises: a flexible insertion section which is to be inserted into an examinee for observation and treatment of an affected portion of the examinee; and an operation section which is operated to bend the insertion section in a UD direction and an RL direction. The operation section includes a UD angle knob for performing an operation in the UD direction and an RL angle knob for performing an operation in the RL direction. When an affected portion is observed or treated, the insertion section can be curved in both the UD direction and the RL direction by operating the UD angle knob and the RL angle knob.

Some endoscopes employ a motor to drive a bending portion in the UD direction and RL direction. For example, in the endoscope described in International Publication No. 2013-129494, an insertion section is manually curved in the up and down (UD) direction, and is automatically curved by a motor in the right and left (RL) direction. The operation section is provided with a knob for an operation in the up and down (UD) direction and a dial for an operation in the right and left (RL) direction.

BRIEF SUMMARY OF THE INVENTION

One embodiment of the present invention is a dial unit comprising a dial member including a shaft and being rotatable around the shaft, a detector which detects a rotation amount of the dial member, a rotator engaged with the dial member and rotatable together with the dial member, a first rotation transmission member interposed between the dial member and the rotator and configured to keep separate the dial member and the rotator separated from each other before the rotation angle of the dial member reaches a first predetermined angle and to transmit rotation of the dial member to the rotator when the rotation angle of the dial member exceeds the first predetermined angle; and an elastic member which is shaped as a coil-shaped portion and contains the rotator inside the coil-shaped portion and which is configured to apply to the rotator a torque in an opposite direction to a rotational direction of the rotator when the rotator rotates.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

First Embodiment

Figure 1:
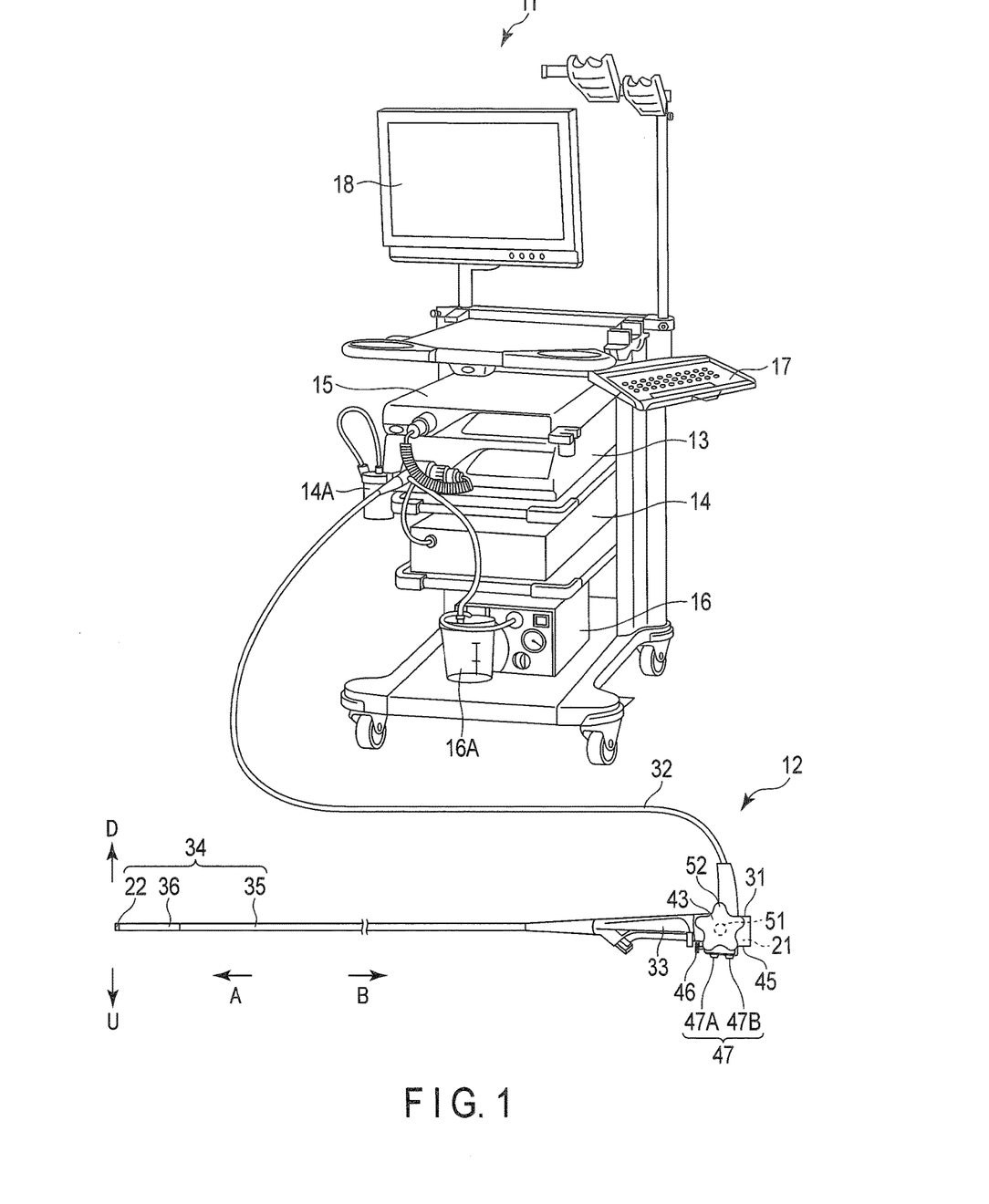
FIG. 1 is a perspective view showing the entire structure of an endoscope apparatus according to an embodiment.

FIG. 1 shows the entire structure of an endoscope apparatus according to the present invention. As shown in FIG. 1, the endoscope apparatus 11 comprises an endoscope 12, a light source apparatus 13, a controller 15 which performs control including image processing, a water supply apparatus 14 such as a water supply pump, a suction apparatus 16 such as a suction pump, a keyboard 17, a monitor 18, and an actuator section 21.

Under the control of the controller 15, the light source apparatus 13 supplies light to an illumination lens 23, located at a distal rigid portion 22 (mentioned later) of the endoscope 12. Under the control of the controller 15, the water supply apparatus 14 supplies a liquid from a water tank 14A to a nozzle 24 which is arranged at the distal rigid portion 22 of the endoscope 12. The suction apparatus 16 sucks a liquid, a tissue or the like from a living body through a channel 44 and collects the sucked liquid or tissue in a waste tank 16A. The image processor (not shown) of the controller 15 performs image processing for an image of an examinee photographed through an objective lens 25 of the distal rigid portion 22 of the endoscope 12, and displays the image on the monitor 18.

The controller 15 is connected to a detector 27 of a second dial unit 46 of an operation section (to be mentioned later) of the endoscope 12. The detector 27 detects a rotation direction and a rotation amount of a dial member 28 of the second dial unit 46, and supplies a detection signal to the controller 15. The controller 15 drives the actuator section 21 of the operation section 31 in accordance with the rotation amount detected by the detector 27, and curves a bending portion 36 in the R direction and L direction.

As shown in FIG. 1, the endoscope 12 comprises an operation section 31, a universal code 32 for coupling the operation section 31 and the light source apparatus 13, a grip section 33 adjacent to the operation section 31, and an introduction section 34 extending from the grip section 33 and configured to be introduced into a cavity (examinee). The endoscope 12 is an example of the introduction apparatus. The endoscope 12 is connected to the controller 15, light source apparatus 13, and water supply apparatus 14 and suction apparatus 16 by means of the universal code 32.

In FIG. 1, arrow A indicates the direction toward the longitudinal distal end, and arrow B indicates the direction toward the longitudinal proximal end. The introduction section 34 includes a soft portion 35 which is elongated and flexible, a bending portion 36 located at the distal end of the soft portion 35, and a distal rigid portion 22 located at the distal end of the bending portion 36.

Figure 3:
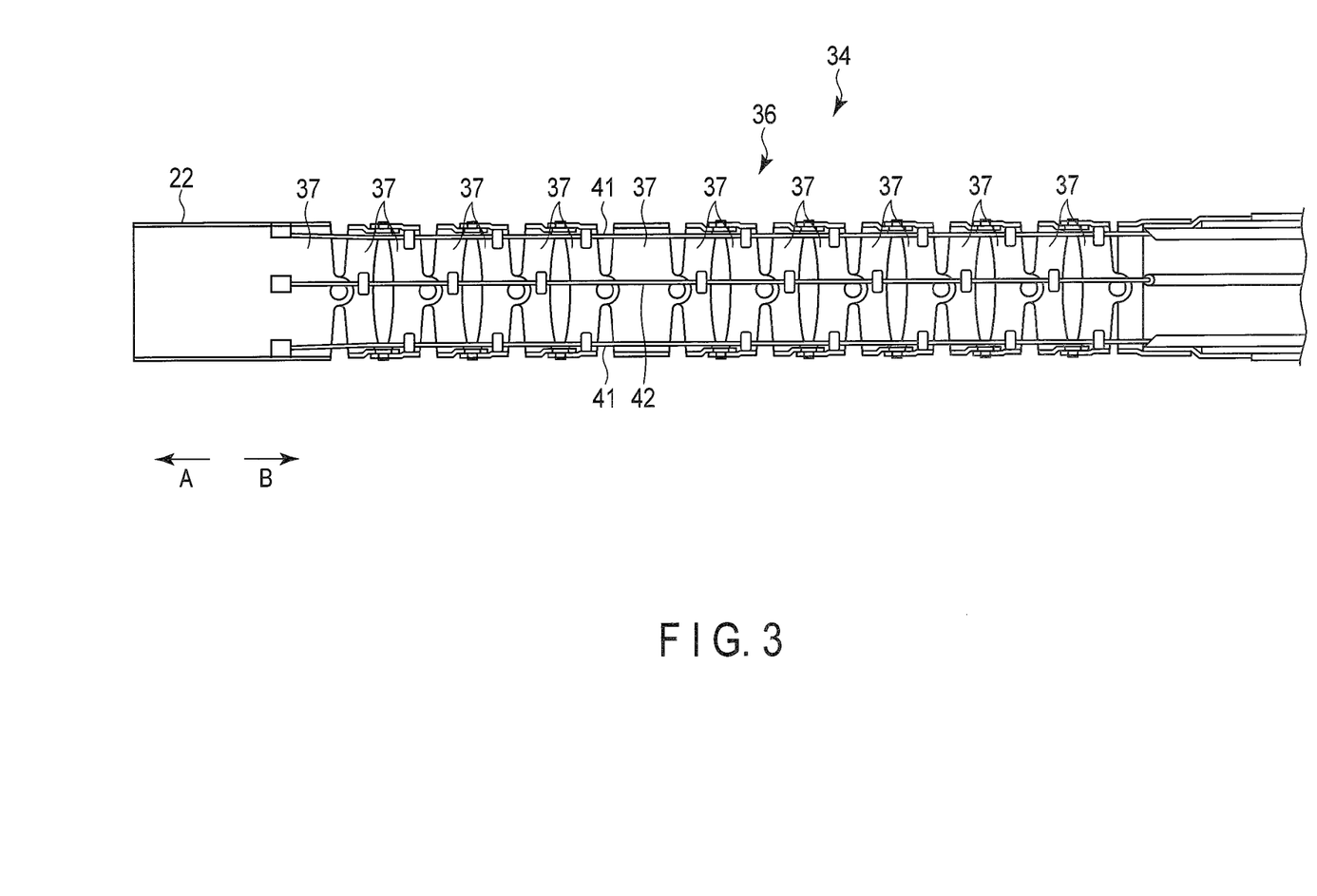
FIG. 3 is a sectional view of bending pieces and first and second wires employed in the endoscope apparatus depicted in FIG. 1.

As shown in FIG. 3, the soft portion 35 and the bending portion 36 contain a plurality of bending pieces 37 arranged along the longitudinal axis C of the introduction section 34. A pair of first wires 41 for permitting the bending portion 36 to bend in a U direction or in a D direction opposite thereto, and a pair of second wires 42 for permitting the bending portion 36 to bend in an R direction or in an L direction opposite thereto, are inserted through the bending pieces 37. The pair of first wires 41 and the pair of second wires 42 are fixed to the bending piece 37 located at the most distal end of the introduction section 34. The pair of first wires 41 is fixed to a pulley of a first dial unit 43 on the side of the operation section 31. Likewise, the pair of second wires 42 is fixed to a pulley of the second dial unit 46 on the side of the operation section 31. The bending pieces 37, first wires 41 and second wires 42 enable the bending portion 36 to bend in the U direction, D direction, R direction, L direction, or any direction obtained by combining these directions.

Figure 2:
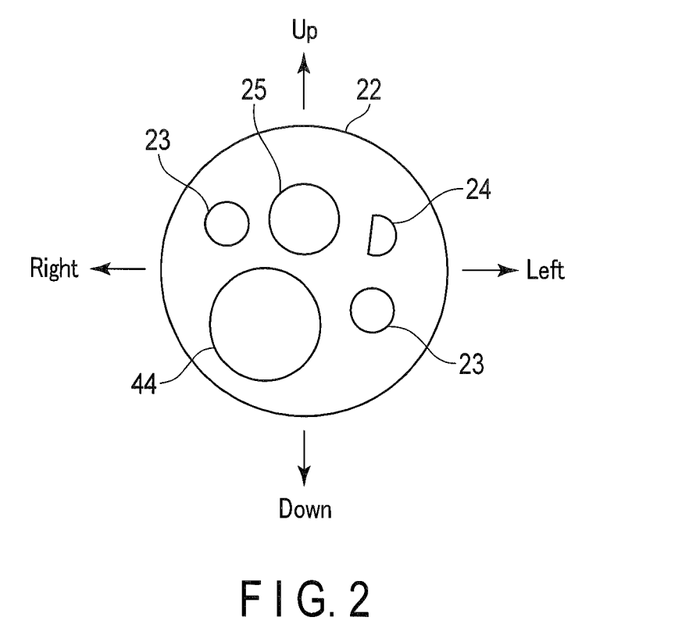
FIG. 2 is a front view showing how a distal rigid portion of the endoscope apparatus looks like when viewed from an end face.

As shown in FIG. 2, the distal rigid portion 22 is provided with an objective lens 25, a treatment tool insertion channel 44, an illumination lens 23, and a nozzle 24. The nozzle 24 is used for supplying water or air with which the distal end face of the distal rigid portion 22 is cleaned and for sucking a liquid and a tissue from a living body.

As shown in FIG. 1, the operation section 31 comprises a case 45 made, for example, of a synthetic resin or the like and defining an internal space, a first dial unit 43 protruded from the case 45 and rotatable relative to the case 45, a second dial unit 46 protruded from the case 45 and rotatable relative to the case 45, a button section 47 provided for the case 45, and an actuator section 21 provided inside the case 45.

The button section 47 includes a first button 47A (an air supply/water supply button) operated when the air or water is supplied to the distal rigid portion 22 of the endoscope 12 through the nozzle 24, and a second button 47B (a suction button S) operated when the distal rigid portion 22 of the endoscope 12 performs suction through the nozzle 24.

The actuator section 21 applies a driving force for curving the bending portion 36 in the R direction and the L direction. The actuator section 21 is made, for example, of a motor such as a servo motor. The driving force of the actuator section 21 is transmitted to the pair of second wires 42 by means of gears, pulleys etc. provided inside the operation section 31.

The first dial unit 43 is provided so that the bending portion 36 can be curved in the U direction (up) or the D direction (down) without using the driving force of the motor. The first dial unit 43 includes a rotating shaft 51, a UD knob 52 fixed to one end of the rotating shaft 51, and a first pulley fixed at the other end of the rotating shaft 51. The pair of first wires is fixed to the first pulley of the first dial unit 43. The UD knob 52 is substantially star-shaped and has five claws, for example. When the user operates the UD knob 52 of the first dial unit 43, the first pulley rotates, pulling one of the first wires 41 and releasing the tension of the other first wire 41. As a result, the bending portion 36 is curved in the U direction or the D direction.

The second dial unit 46 is provided so that the bending portion 36 can be curved in the R direction (right) or the L direction (left) by means of the actuator section 21. That is, the bending portion 36 can be curved in the R direction or the L direction in accordance with the rotation angle of the second dial unit 46. In the present embodiment, the angle by which the bending portion is actually curved is smaller than the angle by which the second dial unit 46 (dial member 28) is rotated from the neutral position.

As shown in FIGS. 4 through 7, the second dial unit 46 comprises: a dial member 28 including a dial main body 53 and a shaft 54; a detector 27 engaged with the dial member 28 and configured to detect a rotation angle (rotation amount) of the dial member 28; a first shaft 55 and a second shaft 56 engaged with the dial member 28 and rotatable with the dial member 28; a first housing 57 surrounding the first shaft 55; a second housing 58 surrounding the second shaft 56; and a bracket member 61 fixed to the case 45.

The second dial unit 46 further comprises: a first O-ring 62 and a second O-ring 63 which are interposed between the dial member 28 and the bracket member 61; a third O-ring 64 which is interposed between the bracket member 61 and the case 45; a first spring 65 interposed between the first shaft 55 and the first housing 57; a second spring 66 interposed between the second shaft 56 and the second housing 58; a first nut 67 fixed to the first shaft 55; a second nut 68 fixed to the second shaft 56; a third nut 71 fixed to the detector 27; a screw 72 fixing the dial main body 53 and the shaft 54 to each other; an adjustment pin 73 contained in the shaft 54 and capable of advancing or retreating; and a plurality of slide pieces 74 which are slidable in radial directions of the shaft 54 by means of the adjustment pin 73.

Figure 5:
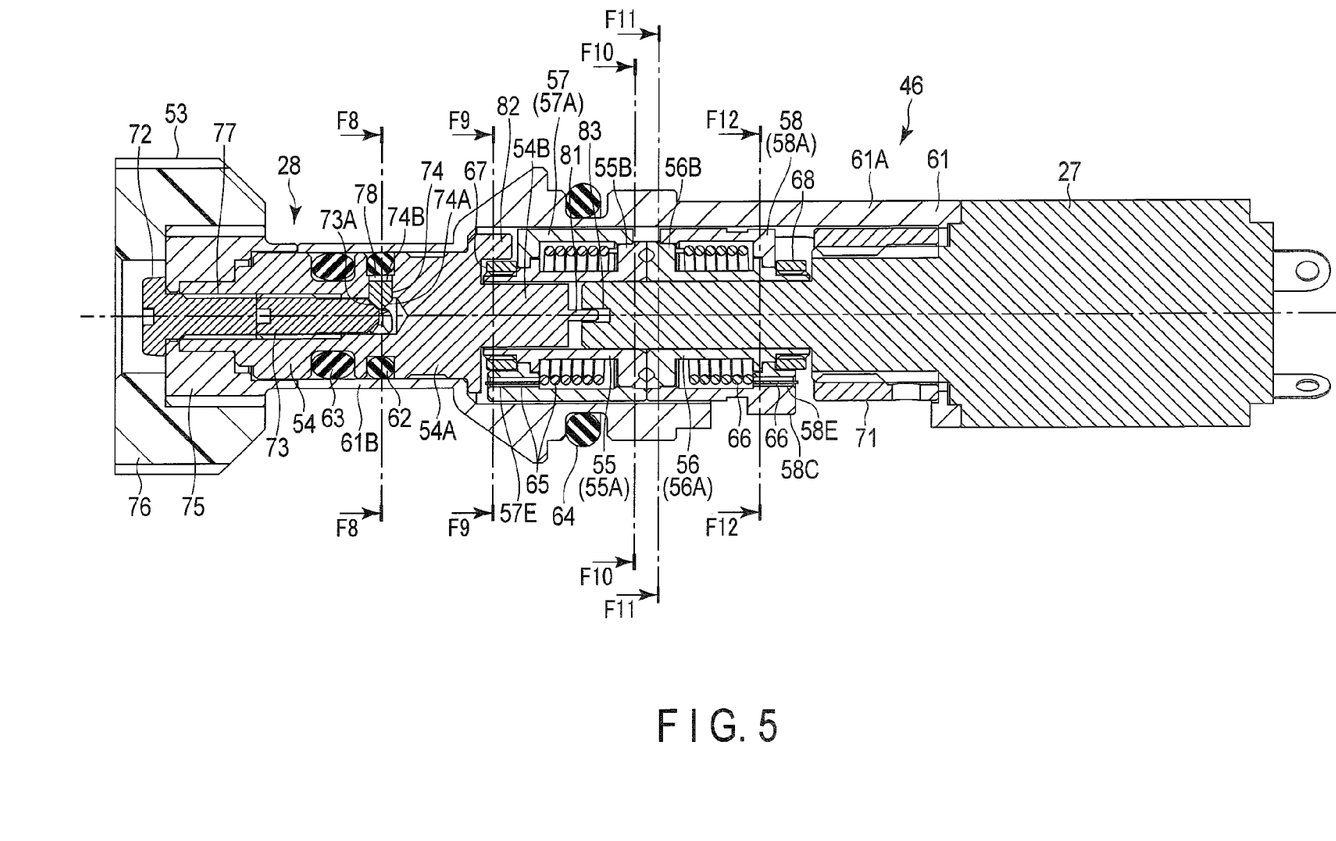
FIG. 5 is a sectional view of the second dial unit depicted in FIG. 4, the sectional view being taken in a plane passing the central axis of the second dial unit.
Figure 6:
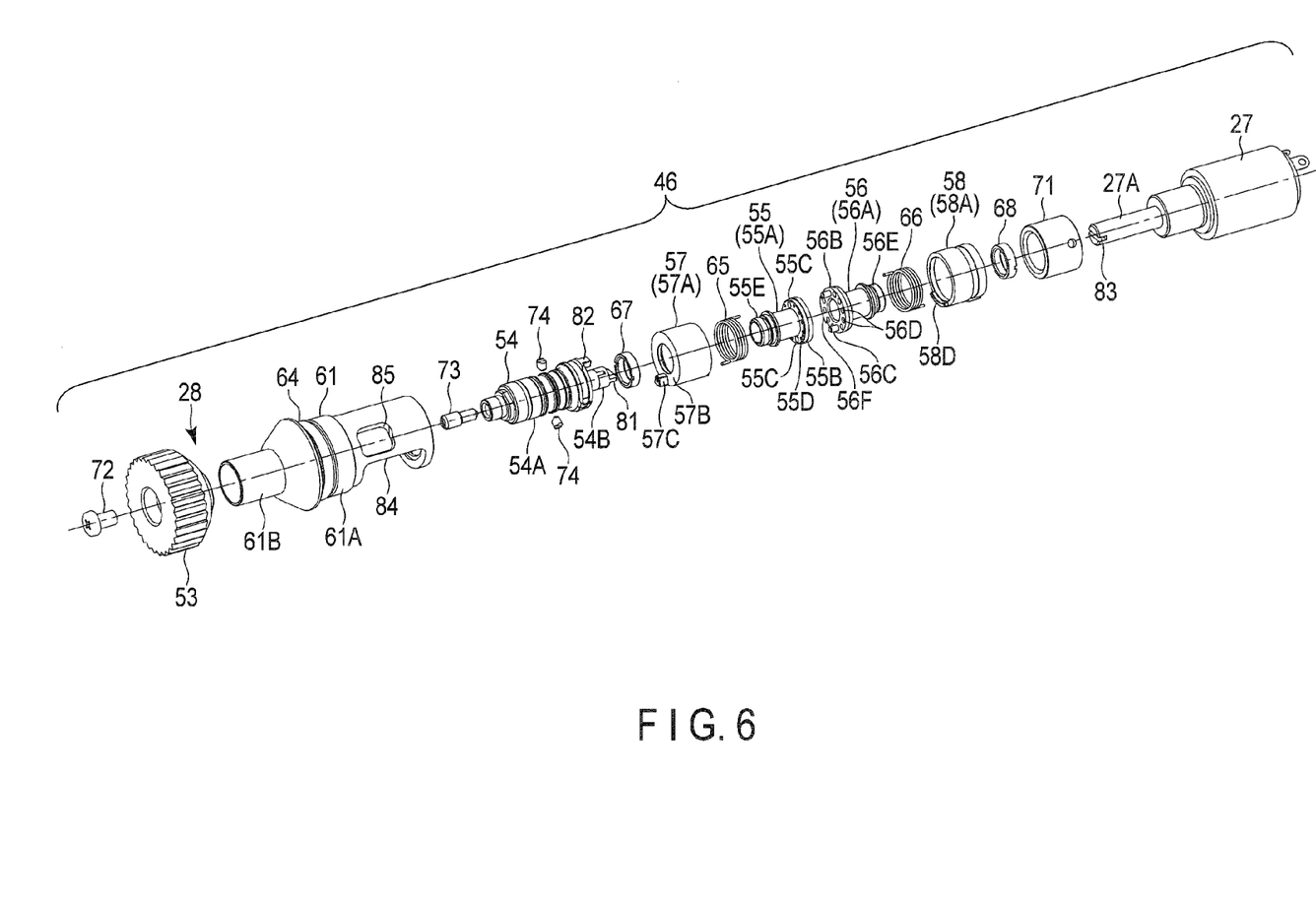
FIG. 6 is a perspective view showing an exploded state of the second dial unit depicted in FIG. 4.
Figure 7:
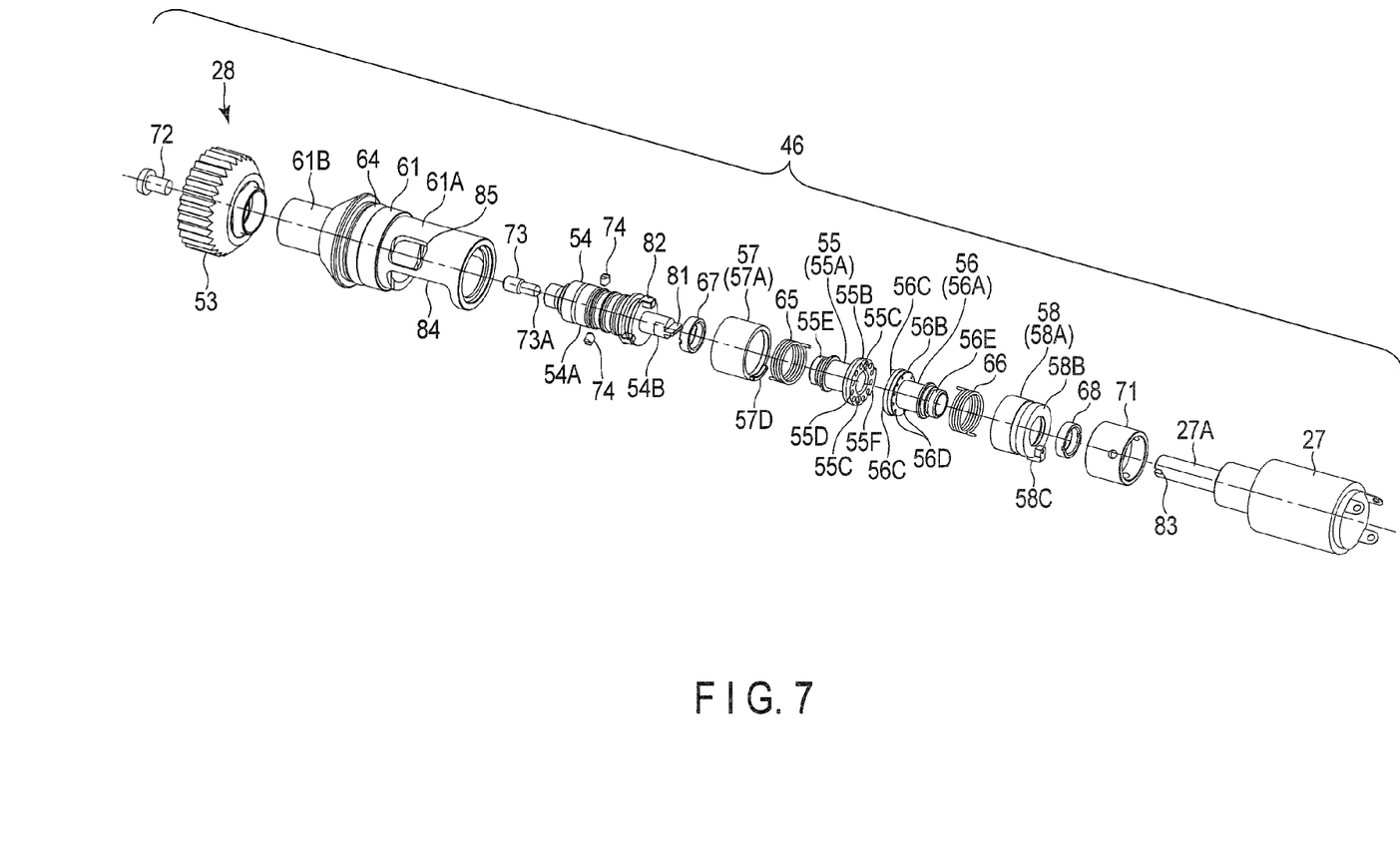
FIG. 7 is a perspective view showing the exploded state of the second dial unit, the exploded state in FIG. 7 being viewed in a direction different from that in FIG. 6.

The dial member 28 can rotate around the shaft 54. The dial main body 53 includes an inner metal portion 75 and an outer resin portion 76. The shaft 54 of the dial member 28 is made of a metallic material and in the form of a rod. The shaft 54 has a step at a position between a proximal end 54A and a distal end 54B. The shaft 54 is fixed to the metallic portion of the dial main body 53 by means of the screw 72. The shaft 54 is provided inside the proximal end 54A. The shaft has a hollow section 77 extending in the extending direction of the shaft 54 and a plurality of through holes 78 (e.g., three through holes) extending in radial directions of the shaft 54 and communicating with the hollow section 77. The adjustment pin 73 can be received in the hollow section 77 of the shaft 54. The shaft 54 includes a claw 81 protruded from the distal end 54B toward the detector 27, and a projection 82 extending from the proximal end 54A toward the detector 27. The metallic rotating shaft 27A of the detector 27 is provided with a slit 83, and the claw 81 can be fitted in the slit 83.

The adjustment pin 73 is a stepped pin whose diameter is smaller at the distal end than at the proximal end. The adjustment pin 73 is made of a metallic material. The adjustment pin 73 has a tapered face at the distal end, which comes into contact with the slide pieces 74. The adjustment pin 73 can be advanced or retreated in the extending direction of the shaft 54 in accordance with the tightening force of the screw 72. Referring to FIG. 5, when the fastening amount of the screw 72 to the shaft 54 is increased, the adjustment pin 73 moves toward the detector 27. Conversely, when the fastening amount of the screw 72 is decreased, the slide pieces 74 move radially inward of the shaft 54 by the tension (repulsive force, elastic force) of the first O-ring 62. In accordance with the movement of the slide pieces 74, the adjustment pin 73 moves toward the dial main body 53, as seen in FIG. 5.

In the present embodiment, the number of slide pieces 74 is three. The slide pieces 74 are fitted in the through holes 78. The three slide pieces 74 are located inside the first O-ring 62. The three slide pieces 74 are identical in shape. Each of the slide pieces 74 has an inclined portion 74A which comes into contact with the tapered face of the adjustment pin 73, and a flat abutment face 74B which comes into contact with the first O-ring 62. Each of the slide pieces 74 is made of a metallic material.

The positions of the slide pieces 74 can be adjusted by means of the adjustment pin 73. To be more specific, when the adjustment pin 73 is moved toward the detector 27 in FIG. 5, the slide pieces 74 move radially outward. Conversely, when the adjustment pin 73 is moved toward the dial main body 53 in FIG. 5, the slide pieces 74 move radially inward of the shaft 54 by the tension of the first O-ring 62. The force with which the first O-ring 62 pushes the bracket member 61 can be controlled by adjusting the positions of the slide pieces 74.

The detector 27 is, for example, a potentiometer, but may be another type of sensor (e.g., a rotary encoder) as long as it can detect a rotation amount of the dial member 28. The detector 27 detects a rotation direction and a rotation amount of the dial member 28 by sensing the rotation angle of the dial member 28.

Figure 10:
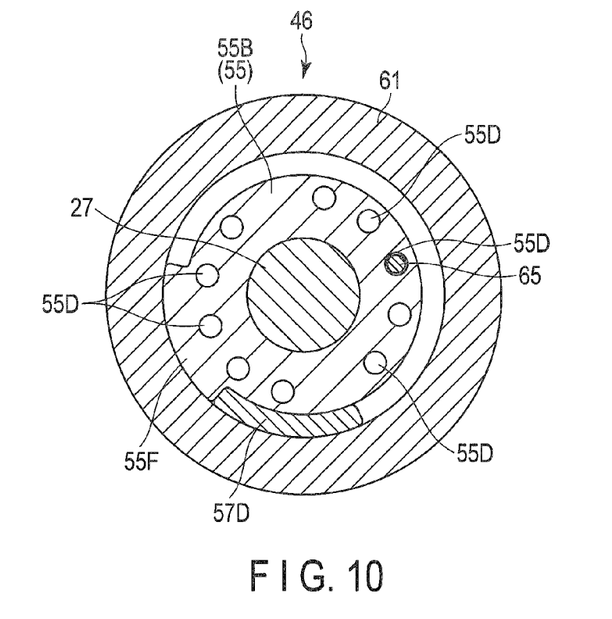
FIG. 10 is a sectional view taken along line F10-F10 shown in FIG. 5.

The first shaft 55 is a cylindrical member with a flange. The first shaft 55 includes: a first shaft main body 55A; a first flange 55B; first holes 55C formed in the first flange 55B and configured to receive pins 56C of the second shaft 56; a second hole 55D formed in the first flange 55B and configured to fix one end of the first spring 65; a first threaded portion 55E provided on the end located on the opposite side of the first flange 55B and configured to fix the first nut 67; and a first protruding piece 55F (see FIGS. 7 and 10) protruded from the first flange 55B radially outward of the first shaft 55. The first shaft 55 is arranged inside the coil-shaped portion of the first spring 65.

Figure 11:
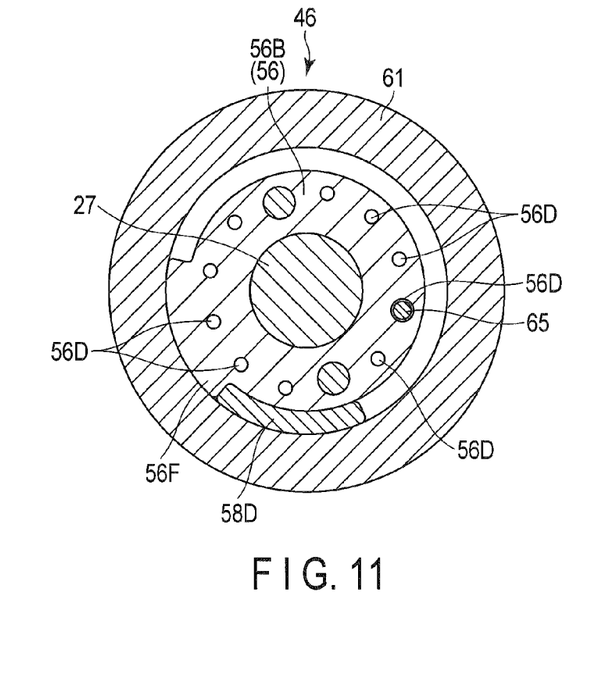
FIG. 11 is a sectional view taken along line F11-F11 shown in FIG. 5.

The second shaft 56 as well as the first shaft 55 is a cylindrical member with a flange. The second shaft 56 includes: a second shaft main body 56A; a second flange 56B which is brought into contact with the first flange 55B; a pair of pins 56C provided on the second flange 56B; a third hole 56D formed in the second flange 56B and configured to fix one end of the second spring 66; a second threaded portion 56E provided on the end located on the opposite side of the second flange 56B and configured to fix the second nut 68; and a second protruding piece 56F (see FIGS. 6 and 11) protruded from the second flange 56B radially outward of the first shaft 55. The first shaft 55 and the second shaft 56 can rotate together, with the pins 56C of the second shaft 56 being inserted into the first holes 55C. The second shaft 56 is arranged inside the coil-shaped portion of the second spring 66. The first shaft 55 and the second shaft 56 are examples of rotators.

The first housing 57 is interposed between the dial member 28 and the first shaft 55 (rotator). The first housing 57 includes a first cylindrical portion 57A, a first end portion 57B projected radially inward from the first cylindrical portion 57A, a first stopper 57C protruded from the first end portion 57B toward the dial member 28, a first through hole 57E formed in the first end portion 57B, and a second stopper 57D protruded in the direction opposite to that in which the dial member 28 is located. The first stopper 57C can come into contact with the projection 82 provided on the shaft 54 of the dial member 28. The second stopper 57D can come into contact with the first protruding piece 55F of the first shaft 55. The other end of the first spring 65 is fixed in the first through hole 57E. The first housing 57 is an example of the first rotation transmission member.

The first spring 65 is made of a so-called right-handed torsion coil spring. In the present embodiment, the first spring 65 is fixed to both the first shaft 55 and the first housing 57 in the elastically deformed state where the first spring 65 is twisted 120° to 160° in advance in the compressed direction. With this structure, the torque which the first spring 65 applies in the direction opposite to the rotating direction of the dial member 28 (i.e., the force with which the dial member 28 returns to the neutral state) is increased.

The second housing 58 is interposed between the second shaft 56 (rotator) and the bracket member 61. The second housing 58 includes a second cylindrical portion 58A, a second end face 58B projected radially inward from the second cylindrical portion 58A, a third stopper 58C protruded outward from the second cylindrical portion 58A and the second end face 58B, a second through hole 58E formed in the second end face 58B, and a fourth stopper 58D protruded in the direction opposite to that in which the detector 27 is located (i.e., in the direction toward the dial member 28). The third stopper 58C can come into contact with an edge portion 87 of the bracket member 61. The fourth stopper 58D can come into contact with the second protruding piece 56F of the second shaft 56. The other end of the second spring 66 is fixed in the second through hole 58E. The second housing 58 is an example of the second rotation transmission member.

The second spring 66 is made of a so-called left-handed torsion coil spring. The second spring 66 as well as the first spring 65 is fixed to both the second shaft 56 and the second housing 58 in the elastically deformed state where the second spring 66 is twisted 120° to 160° in advance in the compressed direction. With this structure, the torque which the second spring 66 applies in the direction opposite to the rotating direction of the dial member 28 (i.e., the force with which the dial member 28 returns to the neutral state) is increased. Each of the first spring 65 and the second spring 66 is an example of the coil-shaped elastic member.

The bracket member 61 is substantially cylindrical as a whole and serves as an outer shell of the second dial unit 46. The bracket member 61 includes: a cylindrical portion 61A configured to receive the distal end of the shaft 54 of the dial member 28, part of the detector 27, the first shaft 55, the second shaft 56, the first housing 57, the second housing 58, etc.; and a bearing portion 61B smaller in diameter than the cylindrical portion 61A and configured to receive the base portion 54A of the shaft 54 of the dial member 28. The cylindrical portion 61A is provided with a first opening 84, two second openings 85 adjacent to the first opening 84, a wall portion 86 located between the two second openings 85, and edge portions 87 provided on the wall portion 86 and defining the boundary between the wall portion 86b and the second openings 85. Each of the second openings 85 has a smaller area than the first opening 84.

Figure 8:
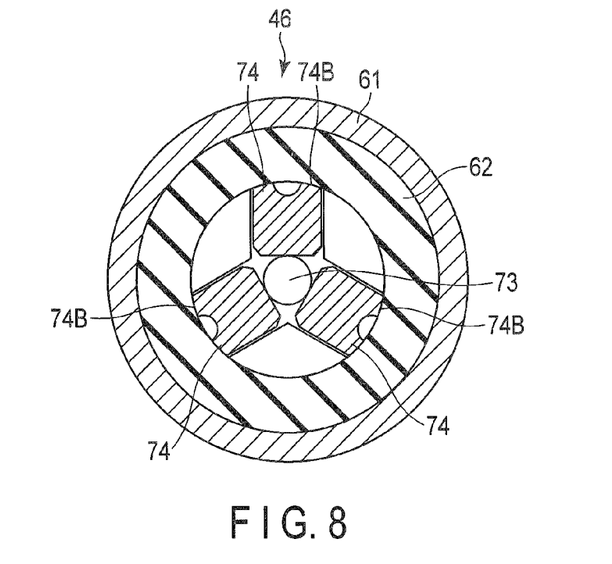
FIG. 8 is a sectional view taken along line F8-F8 shown in FIG. 5.

The first O-ring 62 is made, for example, of silicone rubber and surrounds the proximal end of the shaft 54 at positions outward of the slide pieces 74. In other words, the first O-ring 62 can be regarded as being interposed between the bracket member 61 and the shaft 54 of the dial member 28. As shown in FIG. 8, the first O-ring 62 increases in diameter when the slide pieces 74 move radially outward. In this state, resistance is provided when the shaft 54 of the dial member 28 rotates relative to the bracket member 61. The first O-ring 62 and slide pieces 74 are an example of a resistance provider.

The second O-ring 63 is made, for example, of silicone rubber and surrounds the proximal end of the shaft 54. The second O-ring 63 provides a watertight structure and prevents water from entering through the gap between the bracket member 61 and the shaft 54 of the dial member 28.

The third O-ring 64 is made, for example, of silicone rubber and surrounds the outer circumference of the bracket member 61 in such a manner as to infill the gap between the case 45 of the operation section 31 and the bracket member 61. The third O-ring 64 provides a watertight structure between the case 45 of the operation section 31 and the bracket member 61.

A description will now be given of an operation of the endoscope apparatus 11 of the present embodiment. According to the present embodiment, when the second dial unit 46 rotates more than 360° from the neutral position, the first spring 65 and the second spring 66 return the dial member 28 to the 360° position.

Figure 4:
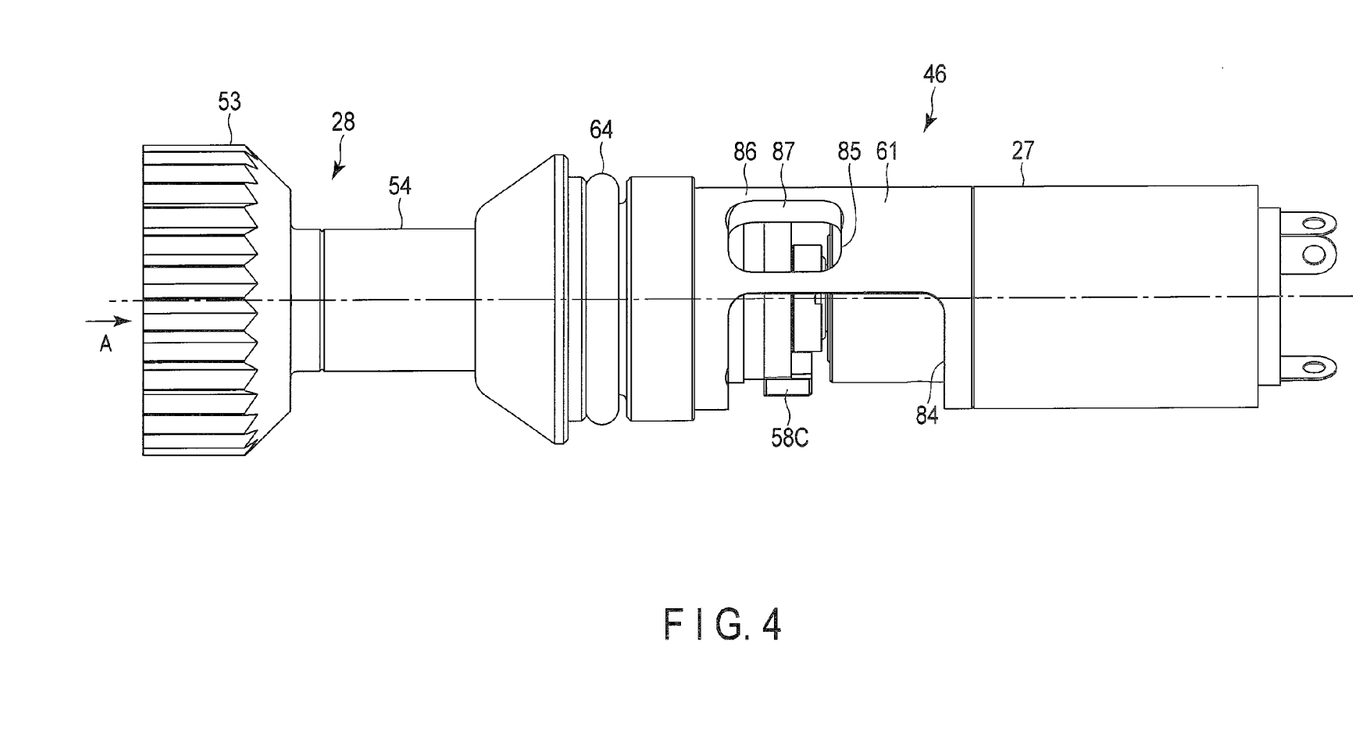
FIG. 4 is a side view of a second dial unit of an operation section of the endoscope apparatus depicted in FIG. 1.
Figure 9:
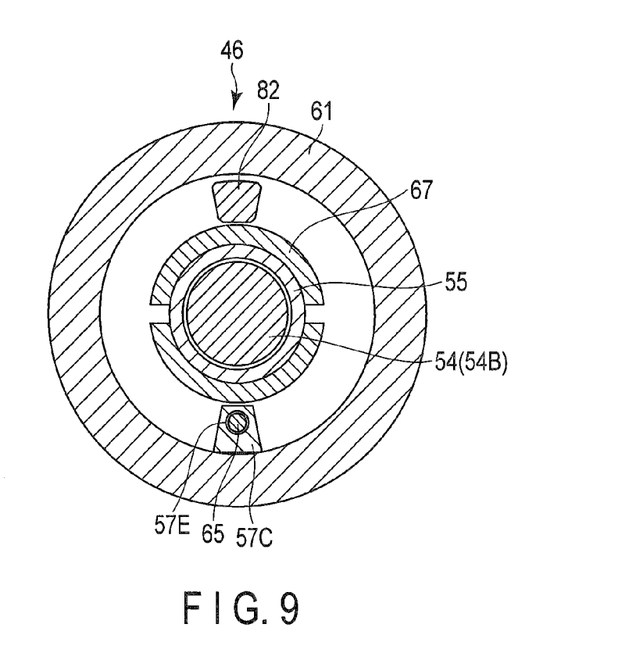
FIG. 9 is a sectional view taken along line F9-F9 shown in FIG. 5.

To curve the bending portion 36 in the R direction, the user rotates the dial member 28 clockwise as viewed from the front face of the dial member (as viewed in the direction of arrow A in FIG. 4). In this case, only the dial member 28 rotates from the neutral position to the substantially 180° position (a first predetermined angle) (a first operation mode). When the dial member 28 has rotated to the substantially 180° position, the projection 82 of the dial member 28 comes into contact with the first stopper 57C of the first housing 57 (see FIG. 9). The clockwise direction is an example of a second direction.

Figure 12:
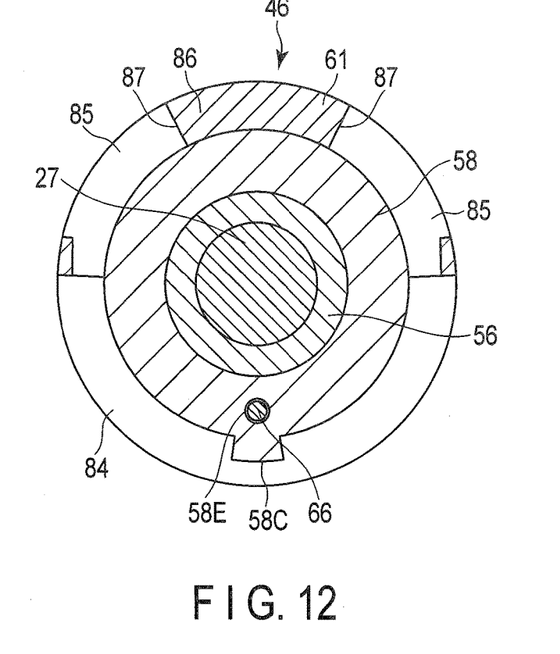
FIG. 12 is a sectional view taken along line F12-F12 shown in FIG. 5.
Figure 13:
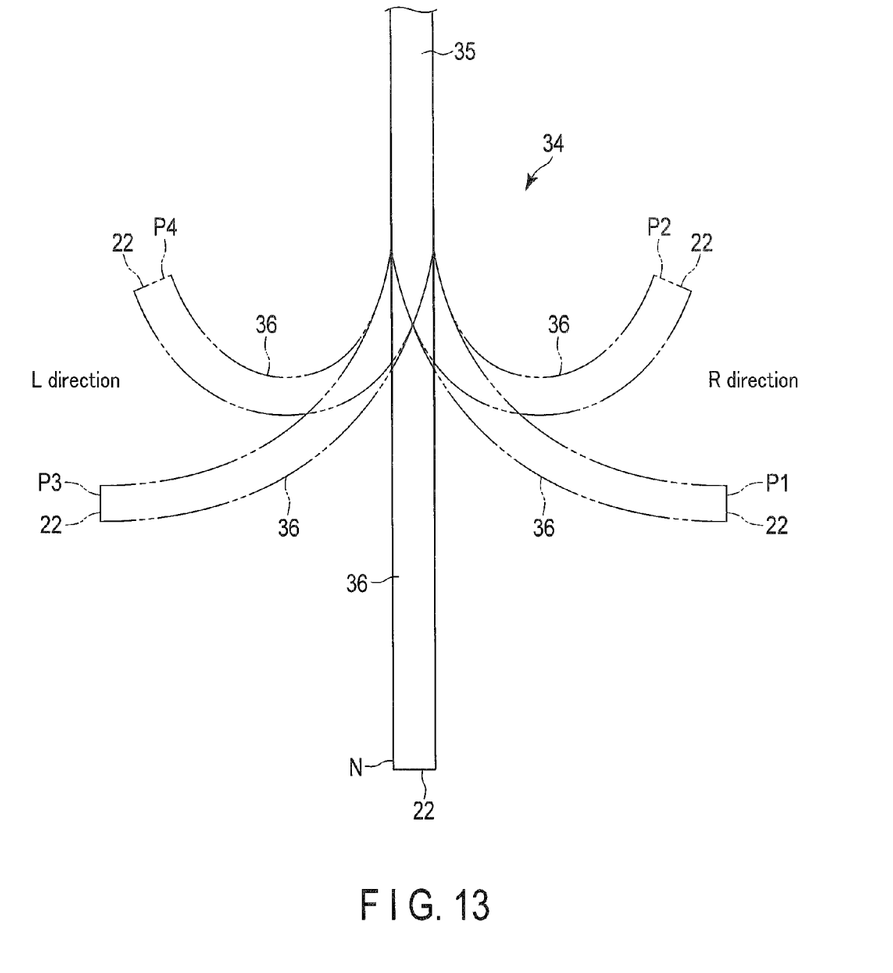
FIG. 13 is a schematic illustration showing how the bending portion is curved in the R direction or the L direction in accordance with the rotation amount of the second dial unit.

When the dial member 28 further rotates clockwise from the 180° position (first predetermined angle) as viewed from the end face of the dial member 28, the dial member 28, the first shaft 55, the second shaft 56, the first housing 57, the second housing 58, the first spring 65 and the second spring 66 rotates integrally (second operation mode). In this state, the rotation of the dial member 28 is transmitted to the first shaft 55 and the second shaft 56 (rotator) by way of the first housing 57 (first rotation transmission member). When the dial member 28 has rotated to the substantially 360° position (second predetermined angle), the third stopper 58C of the second housing 58 (second rotation transmission member) comes into contact with the edge portion 87 of the bracket member 61 (see FIG. 12). As a result, the rotation of the second housing 58 is restricted, and the second housing 58 is prevented from being further rotated clockwise. At the time, the bending portion 36 is curved in the R direction from the neutral position N to the substantially 90° position P1, as shown in FIG. 13.

When the dial member 28 further rotates clockwise from the 360° position (second predetermined angle) as viewed from the end face of the dial member 28, the dial member 28, the first shaft 55, the second shaft 56, the first housing 57, and the first spring 65 rotates integrally (second operation mode). The second housing 58 does not rotate then. Since one end of the second spring 66 is fixed to the second shaft 56 and the other end thereof is fixed to the second housing 58, the second spring 66 is compressed in the spring compression direction (third operation mode). As a result, the second spring 66 applies a torque acting counterclockwise to the dial member 28 rotated clockwise. When the dial member 28 rotates clockwise from the neutral position to the substantially 540° position, against the repulsive force of the second spring 66, the second protruding piece 56F of the second shaft 56 comes into contact with the fourth stopper 58D of the second housing 58, and the dial member 28 is prevented from being further rotated clockwise (see FIG. 11). At the time, the bending portion 36 is curved in the R direction from the neutral position N to the substantially 160° position P2, as shown in FIG. 13.

If the user separates his or her finger from the dial member 28 in the state where the dial member 28 is rotated clockwise from the neutral position to a position in the range of 360° to 540° as viewed from the end face of the dial member 28, the repulsive force of the second spring 66 causes the dial member 28 to return to the position rotated 360° from the neutral position. Since the dial member 28 returns to this position, the bending portion 36 returns in the R direction from the neutral position N to the substantially 90° position P1, as shown in FIG. 13. If it is desired that the bending portion 36 is completely returned to the neutral position N, the user rotates the dial member 28 counterclockwise as viewed in the end face of the dial member 28. As a result, the bending portion 36 returns to the neutral position N.

To curve the bending portion 36 in the L direction, the user rotates the dial member 28 counterclockwise as viewed from the front face of the dial member 28. In this case, only the dial member 28 rotates from the neutral position to the substantially 180° position (a first predetermined angle) (a fourth operation mode). When the dial member 28 has rotated to the substantially 180° position, the projection 82 of the dial member 28 comes into contact with the first stopper 57C of the first housing 57 (see FIG. 9). The counterclockwise direction is an example of a first direction, which is opposite to the second direction mentioned above.

When the dial member 28 further rotates counterclockwise from the substantially 180° position (first predetermined angle) as viewed from the end face of the dial member 28, the dial member 28, the first shaft 55, the second shaft 56, the first housing 57, the second housing 58, the first spring 65 and the second spring 66 rotates integrally (fifth operation mode). In this state, the rotation of the dial member 28 is transmitted to the first shaft 55 and the second shaft 56 (rotator) by way of the first housing 57 (first rotation transmission member). When the dial member 28 has rotated to the substantially 360° position, the third stopper 58C of the second housing 58 (second rotation transmission member) comes into contact with the edge portion 87 of the bracket member 61 (see FIG. 12). As a result, the rotation of the second housing 58 is restricted, and the second housing 58 is prevented from being further rotated counterclockwise. At the time, the bending portion 36 is curved in the L direction from the neutral position N to the substantially 90° position P3, as shown in FIG. 13.

When the dial member 28 further rotates counterclockwise from the 360° position as viewed from the end face of the dial member 28, the dial member 28 and the first housing 57 rotates integrally. The first shaft 55 and the second shaft 56 does not rotate then since the rotation of them is restricted by the fourth stopper 58D.

Since one end of the first spring 65 is fixed to the first shaft 55 and the other end thereof is fixed to the first housing 57, the first spring 65 is compressed in the spring compression direction (sixth operation mode). As a result, the first spring 65 applies a torque acting clockwise to the dial member 28 rotated counterclockwise. When the dial member 28 has rotated counterclockwise to the substantially 540° position, against the repulsive force of the first spring 65, the second stopper 57D of the first housing 57 comes into contact with the first protruding piece 55F of the first shaft 55 (see FIG. 10). At the time, the bending portion 36 is curved in the L direction from the neutral position N to the substantially 160° position P4, as shown in FIG. 13.

If the user separates his or her finger from the dial member in the state where the dial member 28 is rotated counterclockwise from the neutral position to a position in the range of 360° to 540° as viewed from the end face of the dial member 28, the repulsive force of the first spring 65 causes the dial member 28 to return to the position rotated 360° from the neutral position. Since the dial member 28 returns to this position, the bending portion 36 returns in the R direction from the neutral position N to the substantially 90° position P3, as shown in FIG. 13.

The range between position P1 and position P3 is a frequently used in the normal use mode of the endoscope. In other words, in the range from the neutral position N to the right and left 90° positions, the user (doctor) often observes the internal region of a cavity, performs biopsy, or performs treatment or examination, with a treatment tool or examination tool inserted in the treatment tool insertion channel 4. In the present embodiment, therefore, the first spring 65 and the second spring 66 are designed not to produce a repulsive force in the range between position P1 and position P3, and the bending portion 36 is allowed to bend at any angle desired without the repulsive force being applied thereto.

According to the first embodiment, a dial unit comprises: a dial member 28 including a shaft 54 and being rotatable around the shaft 54; a detector 27 which detects a rotation amount of the dial member 28; a rotator engaged with the dial member 28 and rotatable together with the dial member 28; a first rotation transmission member interposed between the dial member 28 and the rotator and configured to keep the dial member 28 and the rotator separated from each other before the rotation angle of the dial member 28 reaches a first predetermined angle and to transmit rotation of the dial member 28 to the rotator when the rotation angle of the dial member 28 exceeds the first predetermined angle; and an elastic member which is shaped as a coil-shaped portion and contains the rotator inside the coil-shaped portion and which is configured to apply to the rotator a torque in an opposite direction to a rotational direction of the rotator when the rotator rotates.

According to this structure, the rotator can be arranged inside the coil-shaped portion of the elastic member. In comparison with the case where the elastic member and the rotator are individually installed, the installation space can be reduced, and the dial unit can be reduced in size. According to the above structure, the rotator rotates and the elastic member applies the rotator with an opposite-direction torque, only when the rotation angle of the dial member 28 is made to exceed the first predetermined angle by the first rotation transmission member. Unless the rotation angle of the dial member 28 exceeds the first predetermined angle, the rotator is not applied with the opposite-direction torque. Thus, the angular range of the rotation of the dial member 28 can include a range in which no torque is applied by the elastic member. With this feature, the dial unit of the present embodiment is advantageously applied to the case where the dial member 28 should be kept at the rotated position if the angle of the rotation of the dial member 28 does not exceed the first predetermined angle and should be returned to the first predetermined angle if the angle of the rotation of the dial member 28 exceeds the first predetermined angle.

The introduction apparatus comprises: an operation section 31 including the dial unit mentioned above; an bendable introduction section 34 extending from the operation section 31 and configured to be introduced into a cavity; and an actuator section 21 which causes the introduction section 34 to curve in accordance with the rotation amount of the dial member 28 detected by a detector 27.

According to this structure, the bending portion 36 can be returned to be within a predetermined angular range only when the rotation angle of the dial member 28 exceeds a certain angle. As long as the dial member 28 is within the predetermined angular range, the user (doctor) can observe the internal region of a cavity, perform biopsy, or perform treatment or examination, with the bending portion 36 kept at the intended curvature. Even though the actuator section 21 is employed for curving the bending portion, the endoscope apparatus of the present embodiment can be operated in the same manner as a conventional manually-curving type endoscope apparatus, and thus ensures easy operation for the doctor. In addition, since the dial unit is small, the operation section 31 can be designed to be small. Accordingly, the doctor can easily operate the introduction apparatus.

The dial unit is provided with a fixed bracket member 61 and a second rotation transmission member interposed between the rotator and the bracket member 61. The second rotation transmission member rotates together with the rotator until the rotation angle of the dial member 28 reaches a second predetermined angle larger than a first predetermined angle. When the rotation angle of the dial member 28 has exceeded the second predetermined angle, the second rotation transmission member engages with the bracket member 61 and therefore stops. If the dial member 28 rotates more than the second predetermined angle, the second rotation transmission member causes the elastic member to apply to the dial member 28 a torque in an opposite direction to a rotational direction of the rotator.

According to this structure, the second rotation transmission member keeps the elastic member from working until the dial member 28 rotates from the first predetermined angle to the second predetermined angle. The elastic member is not allowed to generate a torque until the dial member 28 exceeds the second predetermined angle. Of the angular range of the rotation of the dial member 28, the range from the neutral position to the second predetermined angle is a range in which no torque is applied by the elastic member. With this feature, the dial unit can be advantageously applied to the case where the dial member 28 should be kept at the rotated position, provided that the angle of the rotation of the dial member 28 does not exceed the second predetermined angle.

The rotator is arranged inside the coil-shaped portion in the elastically deformed state in advance, so that the elastic member applies to the rotator an increased torque in an opposite direction to a rotational direction of the rotator. According to this structure, the torque applied by the elastic member can be increased, and a desired returning force can be ensured despite the friction between the rotator and the first rotation transmission member and the friction between the rotator and the second friction transmission member.

The dial unit is provided with a resistance provider which is interposed between the bracket member 61 and the shaft 54 of the dial member 28 and applies a resistance force to the shaft 54 of the dial member 28 being rotated. According to this structure, the resistance provider slows the rotating speed of the dial member 28, and the dial member 28 is prevented from promptly returning to the original position by the rotating force (returning force) of the elastic member.

The elastic member includes: a first spring 65 interposed between the first rotation transmission member and the rotator and configured to apply a torque in an opposite direction to a first direction when the rotator rotates in the first direction; and a second spring 66 interposed between the rotator and the second rotation transmission member and configured to apply a torque in an opposite direction to a second direction when the rotator rotates in the second direction opposite to the first direction. That is, the two springs can be arranged in accordance with the two different-direction rotations of the rotator. In comparison with the case where a single spring is employed, the springs withstand long use and can properly apply, to the rotator, with a returning force for returning the rotator to the neutral position.

The present invention is not limited to the above-described embodiments, and can be modified in various manners in practice, without departing from the gist of the invention. In addition, the endoscope apparatuses described in the foregoing embodiments can be properly combined in such a manner as to create one endoscope apparatus.

In connection with the embodiments, reference was made to the case where an endoscope is employed as an example of an introduction apparatus. Other examples of the introduction apparatus may include an apparatus that does not comprise an illumination optical system (including a light source apparatus and an illumination lens for a distal rigid portion) or an observation optical system (including an image capturing apparatus, a monitor and an objective lens for a distal rigid portion).

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A dial unit comprising:
   a dial member including a shaft and a dial, wherein the dial is rotatable with the shaft;
   a detector which detects a rotation amount of the dial member;
   a rotator engageable with the dial member and rotatable together with the dial member;
   a first rotation transmission member interposed between the dial member and the rotator and configured to keep the dial member and the rotator separated from each other before a rotation angle of the dial member reaches a first predetermined angle and to transmit rotation of the dial member to the rotator when the rotation angle of the dial member exceeds the first predetermined angle; and
   an elastic member which is shaped as a coil-shaped portion and contains the rotator inside the coil-shaped portion and which is configured to apply to the rotator a torque in an opposite direction to a rotational direction of the rotator when the rotator rotates.

2. The dial unit according to claim 1, further comprising:
   a fixed bracket member; and
   a second rotation transmission member interposed between the rotator and the bracket member, wherein the second rotation transmission member rotates together with the rotator until the rotation angle of the dial member reaches a second predetermined angle larger than the first predetermined angle, engages with the bracket member and stops thereby when the rotation angle of the dial member has exceeded the second predetermined angle, and causes the elastic member to apply to the dial member a torque in an opposite direction to a rotational direction of the rotator if the dial member rotates more than the second predetermined angle.

3. The dial unit according to claim 2, wherein the rotator is arranged inside the coil-shaped portion in an elastically deformed state in advance, such that the elastic member applies to the rotator an increased torque in an opposite direction to a rotational direction of the rotator.

4. The dial unit according to claim 3, further comprising:
   a resistance provider which is interposed between the bracket member and the shaft of the dial member and applies a resistance force to the shaft of the dial member being rotated.

5. The dial unit according to claim 4, wherein the elastic member includes:
   a first spring interposed between the first rotation transmission member and the rotator and configured to apply a torque in an opposite direction to a first direction when the rotator rotates in the first direction; and
   a second spring interposed between the rotator and the second rotation transmission member and configured to apply a torque in an opposite direction to a second direction when the rotator rotates in the second direction opposite to the first direction.

6. An introduction apparatus comprising:
   an operation section including the dial unit according to claim 1;
   a bendable introduction section extending from the operation section and configured to be introduced into a cavity; and
   an actuator section which causes the introduction section to curve in accordance with the rotation amount of the dial member detected by the detector.

* * * * *